US006228639B1

(12) United States Patent
Gaitanaris (10) Patent No.: US 6,228,639 B1
(45) Date of Patent: May 8, 2001

(54) VECTORS AND METHODS FOR THE MUTAGENESIS OF MAMMALIAN GENES

(76) Inventor: George A. Gaitanaris, 84 Blakely Ct., #234, Frederick, MD (US) 21702

( * ) Notice: Subject to any disclaimer, the term of this patent is extended or adjusted under 35 U.S.C. 154(b) by 0 days.

(21) Appl. No.: 09/002,046

(22) Filed: Dec. 31, 1997

Related U.S. Application Data

(60) Provisional application No. 60/034,094, filed on Dec. 31, 1996.

(51) Int. Cl.$^7$ ........................................................ C12N 5/00
(52) U.S. Cl. ........................ 435/325; 435/320.1; 435/440; 435/455
(58) Field of Search ............................... 435/320.1, 440, 435/455, 325

(56) References Cited

U.S. PATENT DOCUMENTS

| | | | |
|---|---|---|---|
| 5,364,783 | * 11/1994 | Ruley et al. | 435/235.1 |
| 5,464,758 | * 11/1995 | Gossen et al. | 435/69.1 |
| 5,629,159 | * 5/1997 | Anderson | 435/240.2 |
| 5,654,168 | * 8/1997 | Bujard et al. | 435/69.1 |
| 5,695,995 | * 12/1997 | Weintraub et al. | 435/325 |
| 5,888,981 | 3/1999 | Bujard et al. . | |
| 5,912,411 | 6/1999 | Bujard et al. . | |
| 5,922,601 | 7/1999 | Baetscher et al. . | |
| 5,922,927 | 7/1999 | Bujard et al. . | |

FOREIGN PATENT DOCUMENTS

| | | |
|---|---|---|
| WO 98/14614 | 4/1998 | (WO) . |
| WO 99/07389 | 2/1999 | (WO) . |

OTHER PUBLICATIONS

Eggermont and Proudfoot, "Poly(A) Signals and Transcriptional Pause Sites Combine to Prevent Interference Between RNA Polymerase II Promoter," *The EMBO Journal* 12:2539–2548 (1993).
Friedrich and Soriano, "Insertional Mutagenesis by Retroviruses and Promoter Traps in Embryonic Stem Cells," *Methods in Enzymology* 225:681–701 (1993).
Melchner et al., "Selective Disruption of Genes Expresed in Totipotent Embryonal Stem Cells," *Genes & Development* 6:919–927 (1992).
Scherer et al., "Transcriptional Specificity of the Pluripotent Embryonic Stem Cell," *Cell Growth & Differentiation* 7:1393–1401 (1995).
Levy et al. Nature Biotechnology. vol. 14, pp. 610–614, May 1996.*
Paulus et al. Journal of Virology. vol. 70(3), pp. 62–67, Jan. 1996.*
Miller et al. BioTechniques. vol. 7(9), pp. 980–990, 1989.*
Morgan et al. Advanced Drug Delivery Reviews. vol. 12, pp. 143–158, 1993.*
Friedrich et al. Genes & Development. vol. 5, pp. 1513–1523, 1991.*
Heim et al. Proceedings of the National Academy of Sciences, U.S.A. vol. 91, pp. 12501–12504, Dec. 1994.*
Davis et al. Nature. vol. 314, pp. 550–553, Apr. 1985.*
Rijkers, T. et al., "Insertional mutagenesis in transgenic mice," Transgenic Research 3: 203–215, 1994.
Adra et al., "Cloning and expression of the mouse pgk–1 gene and the nucleotide sequence of its promoter," Gene 60:65–74 (1987).
Allende et al., "Insertional mutagenesis in zebrafish identifies two novel genes, pescadillo and dead eye, essential for embryonic development," Genes Dev. 10:3141–3155 (1996).
Altman, S., "Commentary—RNA enzyme–directed gene therapy," Proc. Natl. Acad. Sci. USA 90:10898–10900 (1993).
Ashfield et al., "Transcriptional termination between the closely linked human complement genes C2 and Factor B: common termination factor for C2 and c–myc?" The EMBO Journal 10(13):4197–4207 (1991).
Balling et al., "Craniofacial Abnormalities Induced by Ectopic Expression of the Homeobox Gene Hox–1.1 in Transgenic Mice," Cell 58:337–347 (1989).
Ballinger and Benzer, "Targeted gene mutations in Drosophila," Proc. Natl. Acad. Sci. USA 86:9402–9406 (1989).
Barillot et al., "Theoretical analysis of library screening using a N–dimensional pooling strategy," Nucleic Acids Research 19(22):6241–6247 (1991).
Behringer et al., "Dwarf mice produced by genetic ablation of growth hormone–expressing cells," Genes & Development 2: 453–461 (1988).
Bergemann et al., "Excision of specific DNA–sequences from integrated retroviral vectors via site–specific recombination," Nucleic Acids Research 23(21):4451–4456 (1995).
Bishop, J. M., "Molecular Themes in Oncogenesis," Cell 64:235–248 (1991).
Black et al., "Creation of drug–specific herpes simplex virus type 1 thymidine kinase mutants for gene therapy," Proc. Natl. Acad. Sci. USA 93:3525–3529 (1996).
Borrelli et al., "Transgenic mice with inducible dwarfism," 339:538–541 (1989).
Bradley et al., "Formation of germ–line chimaeras from embryo–derived teratocarcinoma cell lines," Nature 309:255–256 (1984).

(List continued on next page.)

*Primary Examiner*—Remy Yucel
(74) *Attorney, Agent, or Firm*—Clark & Elbing LLP (57) ABSTRACT

Disclosed herein are methods for mutagenizing a mammalian gene, the methods involving introducing into a mammalian cell a retroviral vector which includes a splice acceptor sequence, a transcription termination sequence, and retroviral packaging and integration sequences, the introducing step being carried out under conditions which allow the vector to integrate into the genome of the cell. Also disclosed are retroviral vectors for use in these methods as well as methods for the use of mutagenized cells.

15 Claims, 4 Drawing Sheets

OTHER PUBLICATIONS

Brand and Perrimon, "Targeted gene expression as a means of altering cell fates and generating dominant phenotypes," Development 118:401–415 (1993).

Breitman et al., "Genetic Ablation in Transgenic Mice with an Attenuated Diphtheria Toxin A Gene," Molecular and Cellular Biology 10(2):474–479 (1990).

Breitman et al., "Analysis of lens cell fate and eye morphogenesis in transgenic mice ablated for cells of the lens lineage," Development 106:457–463 (1989).

Breitman et al., "Genetic Ablation: Targeted Expression of a Toxin Gene Causes Microphthalmia in Transgenic Mice," Science 238:1563–1565 (1987).

Bremer et al., "VDE endonuclease cleaves *Saccharomyces cerevisiae* genomic DNA at a single site: physical mapping of the VMA1 gene," Nucleic Acids Research 20(20):5484 (1992).

Brenner et al., "Analysis of mammalian cell genetic regulation in situ by using retrovirus–derived 'portable exons' carrying the *Escherichia coli* lacZ gene," Proc. Natl. Acad. Sci. USA 86:5517–5521 (1989).

Burns et al., "Large–scale analysis of gene expression, protein localization, and gene disruption in *Saccharomyces cerevisiae*," Genes & Development 8:1087–1105 (1994).

Capecchi, M. R., "Altering the Genome by Homologous Recombination," Science 244:1288–1292 (1989).

Cepko et al., "Lineage Analysis Using Retrovirus Vectors," Methods in Enzymology 225:933–960 (1993).

Chalfie et al., "Green Fluorescent Protein as a Marker for Gene Expression," Science 263:802–805 (1994).

Cheng et al., "Use of green fluorescent protein variants to monitor gene transfer and expression in mammalian cells," Nature Biotechnology 14:606–609 (1996).

Choulika et al., "Transfer of Single Gene–Containing Long Terminal Repeats into the Genome of Mammalian cells by a Retroviral Vector Carrying the cre Gene and the loxP Site," Journal of Virology 70(3):1792–1798 (1996).

Chun and Goebl, "The Identification of Transposon–Tagged Mutations in Essential Genes that Affect Cell Morphology in *Saccharomyces cerevisiae*," Genetics 142:39–50 (1996).

Collins, F. S., "Ahead of schedule and under budget: The Genome Project passes its fifth birthday," Proc. Natl. Acad. Sci. USA 92:10821–10823 (1995).

Copp, A. J., "Death before birth: clues from gene knockouts and mutations," Trends in Genetics 11(3):87–93 (1995).

Counter et al., "Telomerase activity in human ovarian carcinoma," Proc. Natl. Acad. Sci. USA 91:2900–2904 (1994).

Dalby et al., "An Inverse PCR Screen for the Detection of P Element Insertions in Cloned Genomic Intervals in *Drosophila melanogaster*," Genetics 139:757–766 (1995).

Das et al., "Upstream regulatory elements are necessary and sufficient for transcription of a U6 RNA gene by RNA polymerase III," The EMBO Journal 7(2):503–512 (1988).

de Lange, T., "Commentary—Activation of telomerase in a human tumor," Proc. Natl. Acad. Sci. USA 91:2882–2885 (1994).

Dymecki, S. M., "Flp recombinase promotes site–specific DNA recombination in embryonic stem cells and transgenic mice," Proc. Natl. Acad. Sci. USA 93:6191–6196 (1996).

Dzierzak et al., "Thy–1 tk transgenic mice with a conditional lymphocyte deficiency," International Immunology 5(8):975–984 (1993).

Evans and Lewis, "Physical mapping of complex genomes by cosmid multiplex analysis," Proc. Natl. Acad. Sci. USA 86: 5030–5034 (1989).

Evans and Kaufman, "Establishment in culture of pluripotential cells from mouse embryos," Nature 292:154–156 (1981).

Ewald et al., "Time–Sensitive Reversal of Hyperplasia in Transgenic Mice Expressing SV40 T Antigen," Science 273:1384–1386 (1996).

Forrester et al., "An induction gene trap screen in embryonic stem cells: Identification of genes that respond to retinoic acid in vitro," Proc. Natl. Acad. Sci. USA 93:1677–1682 (1996).

Frankel et al., "Role of Arginine 180 and Glutamic Acid 177 of Ricin Toxin A Chain in Enzymatic Inactivation of Ribosomes," Molecular and Cellular Biology 10:6257–6263 (1990).

Frankel et al., "Selection and Characterization of Ricin Toxin A–Chain Mutations in *Saccharomyces cerevisiae*," Molecular and Cellular Biology 9(2):415–420 (1989).

Friedrich and Soriano, "Promoter traps in embryonic stem cells: a genetic screen to identify and mutate developmental genes in mice," Genes & Development 5:1513–1523 (1991).

Goodwin and Rottman, "The 3'–Flanking Sequence of the Bovine Growth Hormone Gene Contains Novel Elements Required for Efficient and Accurate Polyadenylation," The Journal of Biological Chemistry 267(23):16330–16334 (1992).

Gossen et al., "Transcriptional Activation by Tetracyclines in Mammalian Cells," Science 268:1766–1769 (1995).

Gossler et al., "Mouse Embryonic Stem Cells and Reporter Constructs to Detect Developmentally Regulated Genes," Science 244:463–465 (1989).

Green and Olson, "Systematic screening of yeast artificial–chromosome libraries by use of the polymerase chain reaction," Proc. Natl. Acad. Sci. USA 87:1213–1217 (1990).

Gu et al., "Deletion of a DNA Polymerase β Gene Segment in T Cells Using Cell Type—Specific Gene Targeting," Science 265:103–106 (1994).

Halder et al., "Induction of Extopic Eyes by Targeted Expression of the eyeless gene in Drosophila," Science 267:1788–1792 (1995).

Hansbrough et al., "A Transgenic Mouse Model for Studying the Lineage Relationships and Differentiation Program of Type II Pneumocytes at Various Stages of Lung Development," The Journal of Biological Chemistry 268(13):9762–9770 (1993).

Heim et al., "Wavelength mutations and posttranslational autoxidation of green fluorescent protein," Proc. Natl. Acad. Sci. USA 91:12501–12504 (1994).

Heyman et al., "Thymidine kinase obliteration: Creation of transgenic mice with controlled immune deficiency," Proc. Natl. Acad. Sci. U.S.A. 86:2698–2702 (1989).

Hirsch and Vanderslice, "Temperature–Sensitive Developmental Mutants of *Caenorhabditis elegans*," Developmental Biology 49:220–235 (1976).

Hofmann et al., "Rapid retroviral delivery of tetracycline–inducible genes in a single autoregulatory cassette," Proc. Natl. Acad. Sci. USA 93:5185–5190 (1996).

Hunter, T., "Cooperation between Oncogenes," Cell 64:249–270 (1991).

Iida et al., "Inducible Gene Expression by Retrovirus–Mediated Transfer of a Modified Tetracycline–Regulated System," Journal of Virology 70(9):6054–6059 (1996).

Jaenisch, R., "Transgenic Animals," Science 240:1468–1474 (1988).

Jat et al., "Direct derivation of conditionally immortal cell lines from an H–2K$^b$–tsA58 transgenic mouse," Proc. Natl. Acad. Sci. USA 88:5096–5100 (1991).

Jürgens et al., "Genetic analysis of pattern formation in the Arabidopsis embryo," Development Supplement 1:27–38 (1991).

Kaiser et al., "'Site–selected' transposon mutagenesis of Drosophila," Proc. Natl. Acad. Sci. USA 87:1686–1690 (1990).

Kalnins et al., "Sequence of the lacZ gene of *Escherichia coli*," The EMBO Journal 2(4):593–597 (1983).

Kessel et al., "Variations of Cervical Vertebrae after Expression of a Hox–1.1 Transgene in Mice," Cell 61:301–308 (1990).

King et al., "Insertion Mutagenesis of Embryonal Carcinoma Cells by Retroviruses," Science 228:554–558 (1985).

Kratochwil et al., "Retrovirus–Induced Insertional Mutation in Mov13 Mice Affects Collagen I Expression in a Tissue–Specific Manner," Cell 57:807–816 (1989).

Kuehn et al., "A potential animal model for Lesch—Nyhan syndrome through introduction of HPRT mutations into mice," Nature 326:295–298 (1987).

Kühn et al., "Inducible Gene Targeting in Mice," Science 269:1427–1429 (1995).

Kunes and Steller, "Ablation of Drosophila photoreceptor cells by conditional expression of a toxin gene," Genes & Development 5:970–983 (1991).

Kwiatkowsi Jr. et al., "Rapid identification of yeast artificial chromosome clones by matrix pooling and crude lysate PCR," Nucleic Acids Research 18(23):7191–7192 (1990).

Landel et al., "Lens–specific expression of recombinant ricin induces developmental defects in the eyes of transgenic mice," Genes & Development 2:1168–1178 (1988).

Levitt et al., "Definition of an efficient synthetic poly(A) site," Genes & Development 3:1019–1025 (1989).

Levy et al., "Retroviral transfer and expression of a humanized, red–shifted green fluorescent protein gene into human tumor cells," Nature Biotechnology 14:610–614 (1996).

Lipshutz et al., "Using Oligonucleotide Probe Arrays to Access Genetic Diversity," BioTechniques 19(3):442–447 (1995).

Liu and Altman, "Inhibition of viral gene expression by the catalytic RNA subunit of Rnase P from *Escherichia coli*," Genes & Development 9:471–480 (1995).

Lu et al., "Retroviral Insertional Mutagenesis as a Strategy for the Identification of Genes Associated with cis–Diamminedichloroplatinum(II) Resistance," Cancer Research 55:1139–1145 (1995).

Mayer et al., "Mutations affecting body organization in the Arabidopsis embryo," Nature 353:402–406 (1991).

Moffat et al., "Inducible cell ablation in Drosophila by cold–sensitive ricin A chain," Development 114:681–687 (1992).

Morgan et al., "Retroviral vectors containing putative internal ribosome entry sites: development of a polycistronic gene transfer system and applications to human gene therapy," Nucleic Acids Research 20(6):1293–1299 (1992).

Mortensen et al., "Production of Homozygous Mutant ES Cells with a Single Targeting Construct," Molecular and Cellular Biology 12(5):2391–2395 (1992).

Mueller and World, "In Vivo Footprinting of a Muscle Specific Enhancer by Ligation Mediated PCR," Science 246:780–786 (1989).

Nagy and Rossant, "Perspectives Series: Molecular Medicine in Genetically Engineered Animals. Targeted Mutagenesis: Analysis of Phenotype without Germ Line Transmission," J. Clin. Invest. 97(6):1360–1365 (1996).

Naldini et al., "In Vivo Gene Delivery and Stable Transduction of Nondividing Cells by a Lentiviral Vector," Science 272:263–267 (1996).

Nirenberg and Cepko, "Targeted Ablation of Diverse Cell Classes in the Nervous System in vivo," The Journal of Neuroscience 13(8):3238–3251 (1993).

No et al., "Ecdysone–inducible gene expression in mammalian cells and transgenic mice," Proc. Natl. Acad. Sci. USA 93:3346–3351 (1996).

Nusse, R., "The activation of cellular oncogenes by retroviral insertion," Trends in Genetics 2(9): 244–247 (1986).

Nüsslein–Volhard and Wieschaus, "Mutations affecting segment number and polarity in Drosophila," Nature 287:795–801 (1980).

Ochman et al., "Genetic Applications of an Inverse Polymerase Chain Reaction," Genetics 120:621–623 (1988).

Olson et al., "Know Your Neighbors: Three Phenotypes in Null Mutants of the Myogenic bHLH Gene MRF4," Cell 85:1–4 (1996).

Osborne and Baker, "Movers and shakers: maize transposons as tools for analyzing other plant genomes," Current Opinion in Cell Biology 7:406–413 (1995).

Paulus et al., "Self–Contained, Tetracycline–Regulated Retroviral Vector System for Gene Delivery to Mammalian Cells," Journal of Virology 70(1):62–67 (1996).

Quaife et al., "Pancreatic Neoplasia Induced by ras Expression in Acinar Cells of Transgenic Mice," Cell 48:1023–1034 (1987).

Rajewsky et al., "Prospectives Series: Molecular Medicine in Genetically Engineered Animals. Conditional Gene Targeting," J. Clin. Invest. 98(3):600–603 (1996).

Ramirez–Solis et al., "Chromosome engineering in mice," Nature 378:720–724 (1995).

Reddy et al., "Retrovirus Promoter–Trap Vector to Induce lacZ Gene Fusions in Mammalian Cells," Journal of Virology 65(3):1507–1515 (1991).

Reddy et al., "Fluorescence–activated sorting of totipotent embryonic stem cells expressing developmentally regulated lacZ fusion genes," Proc. Natl. Acad. Sci. USA 89:6721–6725 (1992).

Riley and Grunwald, "Efficient Induction of point mutations allowing recovery of specific locus mutations in zebrafish," Proc. Natl. Acad. Sci. USA 92:5997–6001 (1995).

Robb et al., "The scl gene product is required for the generation of all hematopoietic lineages in the adult mouse," The EMBO Journal 15(16):4123–4129 (1996).

Robberson et al., "Exon Definition May Facilitate Splice Site Selection in RNAs and Multiple Exons," Molecular and Cellular Biology 10(1):84–94 (1990).

Robertson, E. J., "Pluripotential stem cell lines as a route into the mouse germ line," Trends in Genetics 2(1): 9–13 (1986).

Roe et al., "Integration of murine leukemia virus DNA depends on mitosis," The EMBO Journal 12:2099–2108 (1993).

Rosenthal et al., "Genomic walking and sequencing by oligo–cassette mediated polymerase chain reaction," Nucleic Acids Research 18(10):3095–3096 (1990).

Rossant and Nagy, "Genome engineering: the new mouse genetics," Nature Medicine 1(6):592–594 (1995).

Salomon et al., "A Truncated Herpes Simplex Virus Thymidine Kinase Phosphorylates Thymidine and Nucleoside Analogs and Does Not Cause Sterility in Transgenic Mice," Molecular and Cellular Biology 15(10):5322–5328 (1995).

Sandmöller et al., "A Transgenic Mouse Model for Lung Adenocarcinoma," Cell Growth & Differentiation 6:97–103 (1995).

Sauer, B. "Manipulation of Transgenes by Site–Specific Recombination: Use of Cre Recombinase," Methods in Enzymology 225:890–900 (1993).

Scanlon et al., "Genetic Analysis of 63 Mutations Affecting Maize Kernel Development Isolated from Mutator Stocks," Genetics 136:281–294 (1994).

Schnieke et al., "Embryonic lethal mutation in mice induced by retrovirus insertion into the $\alpha 1$(I) collagen gene," Nature 304:315–320 (1983).

Sharma et al., "Differentiation of immortal cells inhibits telomerase activity," Proc. Natl. Acad. Sci. USA 92:12343–12346 (1995).

Sheay et al., "Downstream Insertion of the Adenovirus Tripartite Leader Sequence Enhances Expression in Universal Eukaryotic Vectors," BioTechniques 15(5):856–861 (1993).

Sinn et al., "Coexpression of MMTV/v–Ha–ras and MMTV/c–myc Genes in Transgenic Mice: Synergistic Action of Oncogenes In Vivo," Cell 49:465–475 (1987).

Skarnes et al., "A gene trap approach in mouse embryonic stem cells: the lacZ reporter is activated by splicing, reflects endogenous gene expression, and is mutagenic in mice," Genes & Development 6:903–918 (1992).

Skarnes et al., "Capturing genes encoding membrane and secreted proteins important for mouse development," Proc. Natl. Acad. Sci. USA 92: 6592–6596 (1995).

Solnica–Krezel et al., "Efficient Recovery of ENU–Induced Mutations from the Zebrafish Germline," Genetics 136:1401–1420 (1994).

Soneoka et al., "A transient three–plasmid expression system for the production of high titer retroviral vectors," Nucleic Acids Research 23(4):628–633 (1995).

Soriano et al., "Promoter Interactions in Retrovirus Vectors Introduced into Fibroblasts and Embryonic Stem Cells," Journal of Virology 65(5):2314–2319 (1991).

Soriano et al., "Retroviral Tagging in Mammalian Development and Genetics," in *Mobile DNA* (Chapter 42), eds. D.E. Berg and M. Howe, American Society for Microbiology, Washington, D.C., pp. 927–937 (1989).

Southern and Berg, "Transformation of Mammalian Cells to Antibiotic Resistance with a Bacterial Gene Under Control of the SV40 Early Region Promoter," Journal of Molecular and Applied Genetics 1:327–341 (1982).

Spradling et al., "Gene disruptions using P transposable elements: An integral component of the Drosophila genome project," Proc. Natl. Acad. Sci. USA 92:10824–10830 (1995).

Sundaresan et al., "Patterns of gene action in plant development revealed by enhancer trap and gene trap transposable elements," Genes & Development 9:1797–1810 (1995).

Swain and Coffin, "Mechanism of Transduction by Retroviruses," Science 255:841–845 (1992).

Takahashi et al., "Forward and Reverse Genetic Approaches to Behavior in the Mouse," Science 264:1724–1733 (1994).

Takeuchi et al., "Gene trap capture of a novel mouse gene, jumonji, required for neural tube formation," Genes & Development 9:1211–1222 (1995).

Triglia et al., "A procedure for in vitro amplification of DNA segments that lie outside the boundaries of known sequences," Nucleic Acids Research 16(16):8186 (1988).

Varmus et al., "Retroviruses as Mutagens: Insertion and Excision of a Nontransforming Provirus Alter Expression of a Resident Transforming Provirus," Cell 25:23–36 (1981).

Varmus and Brown, "Retroviruses," in *Mobile DNA* (Chapter 3), eds. D.E. Berg and M. Howe, American Society for Microbiology, Washington, D.C., pp 53–108 (1989).

von Melchner et al., "Selective disruption of genes expressed in totipotent embryonal stem cells," Genes & Development 6:919–927 (1992).

Wagner, R. W., "Gene inhibition using antisense oligodeoxynucleotides," Nature 372:333–335 (1994).

Weiher et al., "Transgenic Mouse Model of Kidney Disease: Insertional Inactivation of Ubiquitously Expressed Gene Leads to Nephrotic Syndrome," Cell 62:425–434 (1990).

Westerman and Leboulch, "Reversible immortalization of mammalian cells mediated by retroviral transfer and site–specific recombination," Proc. Natl. Acad. Sci. USA 93:8971–8976 (1996).

White et al., "Cell Killing by the Drosophila Gene reaper," Science 271:805–807 (1996).

Withers–Ward et al., "Distribution of targets for avian retrovirus DNA integration in vivo," Genes & Development 8:1473–1487 (1994).

Wood et al., "Non–injection methods for the production of embryonic stem cell–embryo chimaeras," Nature 365:87–89 (1993).

Wurst et al., "A Large–Scale Gene–Trap Screen for Insertional Mutations in Developmentally Regulated Genes in Mice," Genetics 139:889–899 (1995).

Yee et al., "A general method for the generation of high–titer, pantropic retroviral vectors: Highly efficient infection of primary hepatocytes," Proc. Natl. Acad. Sci. USA 91:9564–9568 (1994).

Zwaal et al., "Target–selected gene inactivation in *Caenorhabditis elegans* by using a frozen transposon insertion mutant bank," Proc. Natl. Acad. Sci. USA 90:7431–7435 (1993).

* cited by examiner

LTR, long terminal repeats

L, loxP

V, VDE recognition sequence

SA, splice acceptor

IRES, internal ribosome entry site

*rtTA*, reverse tetracycline dependent transactivator pA, polyA addition signal

P, promoter

A, adenovirus tripartite leader sequences

*gfo*, *gfp-neo* hybrid gene

*gfp*, green fluorescent protein

*neo*, neomycin phosphotransferase gene

SPA, synthetic polyA site t, transcription terminator

*PATHWAY ACTIVE ONLY WHEN GENE X IS EXPRESSED

Fig. 3

*PATHWAY ACTIVE ONLY WHEN GENE X IS EXPRESSED

Fig. 4

VECTORS AND METHODS FOR THE MUTAGENESIS OF MAMMALIAN GENES

CROSS REFERENCE TO RELATED APPLICATIONS

This application claims benefit from provisional application, U.S. Ser. No. 60/034,094, filed Dec. 31, 1996.

BACKGROUND OF THE INVENTION

This invention relates to retroviral vectors and their use in methods of mammalian gene mutagenesis.

Eukaryotic genomes are estimated to contain 6,000–80,000 genes (Collins, Proc. Natl. Acad. Sci. USA 92:10821–10823 (1995)). Even in the best characterized organisms, the function of the majority of these genes is unknown. In addition, relatively little information is available concerning the fraction of the genome that is expressed in particular cell types or the cellular processes in which specific gene products participate. In an attempt to decipher genes' functions, large scale mutagenesis screens have been developed and have proven instrumental in unraveling the roles of certain genes in organisms such as *Drosophila melanogaster* (Nusslein-Volhard and Wieschaus, Nature 287:795–801 (1980); Ballinger and Benzer, Proc. Natl. Acad. Sci. USA 86:9402–9406 (1989); Kaiser and Goodwin, Proc. Natl. Acad. Sci. USA 87:1686–1690 (1990); and Spradling et al., Proc. Natl. Acad. Sci. USA 92:10824–10830 (1995)), *Caenorhabditis elegans* (Hirsh and Vanderslice, Dev Biol. 49:220–235 (1976); and Zwaal et al., Proc. Natl. Acad. Sci. USA 90:7431–7435 (1993)), Zebrafish (Solnica-Krezel et al., Genetics 136:1401–1420 (1994); and Riley and Grunwald, Proc. Natl. Acad. Sci. USA 92:5997–6001 (1995)), Arabidopsis (Jurgens et al., Development Suppl. 1:27–38 (1991); Mayer et al., Nature 353:402–407 (1991); and Sundaresan et al., Genes Dev. 9:1797–1810 (1995)), Maize (Scanlon et al., Genetics 136:281–294 (1994); and Osborne and Baker, Curr. Opin. Cell Biol. 7:406–413 (1995)), and *Saccharomyces cerevisiae* (Burns et al., Genes Dev. 8: 1087–1105 (1994); and Chun and Goebl, Genetics 142:30–50 (1996)). In mammals, however, these approaches have generally been limited by the large genome size and the development of the embryo inside a mother's uterus.

Some progress has been made in understanding mammalian gene function as a result of the development of mouse embryonic stem (ES) cell technology. This technology has significantly altered the field of mammalian genetics by allowing the bulk of genetic manipulations to be executed in vitro (Evans and Kaufman, Nature 292:154–156 (1981); Bradley et al., Nature 309:255–256 (1984); and Robertson, Trends Genet. 2:9–13 (1986)). This is possible because mouse ES cells are pluripotent, that is, they have the ability to generate entirely ES cell-derived animals. Accordingly, gene inactivation in mouse ES cells and subsequent generation of "knock-out" (KO) mice is a powerful method for gaining information about the function of a gene in a whole animal system. If desired, genetic alterations, such as gene KOs which inactivate genes, may be introduced into these cells, and their consequences may be studied in the whole animal (Jaenisch, Science 240:1468–1474 (1988); and Rossant and Nagy, Nat. Med. 1:592–594 (1995)).

Currently, the available mouse mutagenesis methodologies are somewhat limited in their general utility as gene function screening systems. Gene targeting, the most widely used approach, is laborious and time consuming (Capecchi, Science 244:1288–1292 (1989)). And gene trap and chemical/radiation induced mutagenesis are generally restricted in their targets (Gossler et al., Science 244:463–465 (1989); Friedrich and Soriano, Genes Dev. 5:1513–1523 (1991); Skarnes et al., Genes Dev. 6:903–918 (1992); von Melchner et al., Genes Dev. 6:919–927 (1992); Reddy et al., Proc. Natl. Acad. Sci. USA 89:6721–6725 (1992); Takeuchi et al., Genes Dev. 9:1211–1222 (1995); and Takahashi et al., Science 264:1724–1733 (1994)). The gene trap approach is limited to genes expressed in ES cells, although variations of the method have been developed for targeting specific subclasses of genes expressed in early embryonic stages (Wurst et al., Genetics 139:889–899 (1995); Skarnes et al., Proc. Natl. Acad. Sci. USA 92:6592–6596 (1995); and Forrester et al., Proc. Natl. Acad. Sci. USA 93:1677–1682 (1996)). And the chemical/radiation induced mutagenesis technique is generally limited to genes that can result in dominant phenotypes when mutated. None of these approaches, as currently exploited, may be readily streamlined or automated, nor can they be readily adapted to carry out saturated mutagenesis of the mouse genome.

SUMMARY OF THE INVENTION

In general, the invention features a method for mutagenizing a mammalian gene, the method involving introducing into a mammalian cell (for example, a stem cell, such as an embryonic stem cell) a retroviral vector, the vector including a splice acceptor sequence, a transcription termination sequence, and retroviral packaging and integration sequences, the introducing step being carried out under conditions which allow the vector to integrate into the genome of the cell.

In preferred embodiments, the retroviral vector includes packaging and integration sequences derived from a Moloney murine leukemia virus sequence; the retroviral vector further includes a reporter gene whose expression is under the control of a mammalian cell promoter, the promoter being operably linked to the reporter gene upon integration of the vector into the genome of the mammalian cell; the reporter gene encodes a regulatory protein, the regulatory protein being capable of modulating the expression of a detectable gene; the regulatory protein is a tetracycline repressor fused to an activator protein (for example, VP16); the retroviral vector further includes a DNA sequence encoding a constitutively expressed marker gene, the marker gene being detectable in a mammalian cell; the marker gene is a green fluorescent protein (for example, a green fluorescent having increased cellular fluorescence relative to a wild type green fluorescent protein); the green fluorescent protein is fused to a mammalian selectable marker; the mammalian selectable marker encodes neomycin resistance; the retroviral vector further includes a recognition sequence derived from a yeast VDE DNA endonuclease; the retroviral vector further includes a sequence which is recognized by a recombinase enzyme (for example, a loxP sequence); the mammal is a mouse; and the cell is an embryonic stem cell.

In a related embodiment, the invention features a retroviral vector which includes a splice acceptor sequence, a transcription termination sequence, and retroviral packaging and integration sequences. In preferred embodiments, the retroviral vector includes packaging and integration sequences derived from a Moloney murine leukemia virus sequence; the retroviral vector further includes a reporter gene whose expression is under the control of a mammalian cell promoter, the promoter being operably linked to the reporter gene upon integration of the vector into the genome of the mammalian cell; the reporter gene encodes a regulatory protein, the regulatory protein being capable of modulating the expression of a detectable gene; the regulatory protein is a tetracycline repressor fused to an activator protein (for example, VP16); the detectable gene includes an operably linked tetracycline operator; the retroviral vector further includes a DNA sequence encoding a constitutively expressed marker gene, the marker gene being detectable in a mammalian cell; the marker gene is a green fluorescent protein (for example, a green fluorescent protein having increased cellular fluorescence relative to a wild type green fluorescent protein); the green fluorescent protein is fused to a mammalian selectable marker; the mammalian selectable marker encodes neomycin resistance; the retroviral vector further includes a recognition sequence derived from a yeast VDE DNA endonuclease; and the retroviral vector further includes a sequence which is recognized by a recombinase enzyme (for example, a loxP sequence).

In other related embodiments, the invention includes a cell containing a retroviral vector of the invention; a transgenic non-human mammal (for example, a mouse) which includes a retroviral vector of the invention; a library (that is, having at least 100 members) of mutagenized mammalian genes produced by the methods of the invention; and cells (for example, stem cells) which include a library of mutagenized mammalian genes produced by the methods of the invention.

In a related method, the invention features a method for identifying a cell (for example, a stem cell) which includes a retroviral vector, the method involving: (a) introducing into a mammalian cell population a retroviral vector, the vector including a splice acceptor sequence, a transcription termination sequence, retroviral packaging and integration sequences, and a constitutively expressed detectable marker gene, the introducing step being carried out under conditions which allow the vector to integrate into the genomes of the cells; and (b) identifying the cell which includes the retroviral vector by detecting expression of the marker gene.

In preferred embodiments, the marker gene is a green fluorescent protein; and the green fluorescent protein has increased cellular fluorescence relative to the wild-type green fluorescent protein.

In a second related method, the invention features a method for identifying a mutagenized mammalian gene, the method involving: (a) introducing into a mammalian cell (for example, a stem cell) population a retroviral vector, the vector including a splice acceptor sequence, a transcription termination sequence, and retroviral packaging and integration sequences, the introducing step being carried out under conditions which allow the vector to integrate into the genomes of the cells; (b) isolating the genomic DNA from the population of cells; (c) amplifying the genomic DNA using amplification primers based at least in part on the retroviral sequence; and (d) identifying the mutagenized mammalian gene by sequence homology with a wild-type nucleic acid sequence. In a preferred embodiment, the sequence homology is identified using a hybridization technique.

In a third related method, the invention features a method of conditionally ablating a cell lineage, the method involving: (a) providing a first transgenic non-human mammal which includes an activator protein expressed only in the cell lineage; (b) providing a second transgenic non-human mammal which includes a nucleic acid sequence encoding a cell ablation factor, the nucleic acid sequence being under the control of the activator protein and the activator protein being capable of binding to and regulating the nucleic acid sequence only upon induction; (c) mating the first and the second transgenic mammals to produce offspring in which the cell ablation factor is expressed under the control of the activator protein, the cell ablation factor being capable of destroying cells in which it is expressed; and (d) inducing binding and regulation by the activator protein.

In preferred embodiments, the activator protein is introduced into the transgenic non-human mammal on a retroviral vector that includes a splice acceptor sequence, a transcription termination sequence, and retroviral packaging and integration sequences; the activator protein is a tetracycline repressor fused to VP16 and the nucleic acid sequence encoding a cell ablation factor is operably linked to a tetracycline operator; the cell ablation factor is chosen from the group consisting of a toxin, a thymidine kinase, or an apoptotic protein; the conditional induction occurs by administration of tetracycline or a tetracycline derivative to the transgenic mammal; and the mammal is a mouse.

In a fourth related method, the invention features a method for conditional ectopic expression of a gene of interest, the method involving: (a) providing a first transgenic non-human mammal which includes an activator protein expressed under the control of the promoter of an endogenous gene of the mammal; (b) providing a second transgenic non-human mammal which includes a nucleic acid sequence encoding the gene of interest, the nucleic acid sequence being under the control of the activator protein and the activator protein being capable of binding to and regulating the nucleic acid sequence only upon induction; (c) mating the first and the second transgenic mammals to produce offspring in which the gene of interest is expressed under the control of the activator protein; and (d) inducing expression of the activator protein.

In preferred embodiments, the activator protein is introduced into the transgenic non-human mammal on a retroviral vector that includes a splice acceptor sequence, a transcription termination sequence, and retroviral packaging and integration sequences; the activator protein is a tetracycline repressor fused to VP16 and the nucleic acid sequence encoding a cell ablation factor is operably linked to a tetracycline operator; the induction occurs by administration of tetracycline or a tetracycline derivative to the transgenic mammal; and the mammal is a mouse.

In a fifth related method, the invention features a method of generating a nonhuman transgenic mammal having a conditional malignancy, the method involving: (a) providing a first transgenic non-human mammal which includes an activator protein expressed under the control of the promoter of an endogenous gene of the mammal; (b) providing a second transgenic non-human mammal which includes a nucleic acid sequence encoding a neoplastic factor, the nucleic acid sequence being under the control of the activator protein and the activator protein being capable of binding to and regulating the nucleic acid sequence only upon induction; (c) mating the first and the second transgenic mammals to produce offspring in which the neoplastic factor is expressed under the control of the activator protein, the neoplastic factor being capable of promoting the development of the malignancy; and (d) inducing binding and regulation by the activator protein.

In preferred embodiments, the activator protein is introduced into the transgenic non-human mammal on a retroviral vector that includes a splice acceptor sequence, a transcription termination sequence, and retroviral packaging and integration sequences; the activator protein is a tetracycline repressor fused to VP16 and the nucleic acid sequence encoding a cell ablation factor is operably linked to a tetracycline operator; the neoplastic factor is an oncogene; the induction occurs by administration of tetracycline or a tetracycline derivative to the transgenic mammal; and the mammal is a mouse.

The invention also features a cell line derived from one of these transgenic nonhuman mammals, as well as transgenic mosaic non-human mammals generated by the methods of the invention and uses therefor.

In a final related method, the invention features a method for conditional tissue-specific inactivation of a gene of interest, the method involving: (a) providing a first transgenic non-human mammal which includes an activator protein expressed under the control of the promoter of the endogenous gene of interest; (b) providing a second transgenic non-human mammal which includes a ribozyme gene under the control of the activator protein, the ribozyme being capable of specifically interfering with expression of the gene of interest and the ribozyme being produced only upon induction; (c) mating the first and the second transgenic mammals to produce offspring in which the ribozyne is expressed under the control of the activator protein; and (d) inducing expression of the activator protein, whereby the gene of interest is inactivated in cells in which it is endogenously expressed.

In preferred embodiments, the activator protein is introduced into the transgenic non-human mammal on a retroviral vector that includes a splice acceptor sequence, a transcription termination sequence, and retroviral packaging and integration sequences; the activator protein is a tetracycline repressor fused to VP16 and the nucleic acid sequence encoding a ribozyme is operably linked to a tetracycline operator; induction occurs by administration of tetracycline or a tetracycline derivative to the transgenic mammal; and the mammal is a mouse.

The present invention provides a number of advantages. For example, it combines versatile retroviral vectors for ES cell mutagenesis with powerful detection methods for rapid identification of mutant cells of interest. In addition, the method permits mutagenesis in a large number of mammalian genes, in a short period of time, and at a significant reduction in cost. Moreover, the method may be readily streamlined, and many genes may be processed in parallel. Considering that every gene is a potential mutagenesis target, the proposed approach facilitates the generation of extensive libraries of mutated mammalian genes, as well as libraries of pluripotent stem cells carrying those gene mutations.

Other features and advantages of the invention will be apparent from the following detailed description and from the claims.

DETAILED DESCRIPTION

The drawings will first briefly be described.

The present invention involves vectors and a process, termed "MAGEKO" (or "massively parallel gene knock out") which permits the mutagenesis of large numbers of mammalian genes, the creation of libraries containing those mutant genes, and the ready selection from that library of stem cells carrying mutant genes of interest. Although this process is applicable to any mammalian system, it is now described for the generation of mutations and libraries in a mouse system. The following examples are presented for the purpose of illustrating the invention, and should not be construed as limiting.

The MAGEKO Process

The MAGEKO process involves retroviral insertional mutagenesis, on average every 1 Kb in the mouse genome, to create a comprehensive library of KO ("LOK") embryonic stem (ES) cells, and a gene KO identification system ("KIS"). The LOK generally includes mutations in every mouse gene, and the KIS allows the rapid isolation of desired mutant ES cells. The LOK and KIS facilitate the large scale automated search for KO cells potentially corresponding to any desired gene.

Once appropriate ES cells are identified, ES cell-derived embryos are generated in vitro, by aggregation with tetraploid or morulae stage embryos (for example, by the method of Wood et al., Nature 365:87–89 (1993)). These embryos are subsequently implanted into foster mothers for the generation of heterozygotic mice with a KO in the gene of interest. Conventional blastocyst injection methods can also be employed, if appropriate (see, for example, Robertson, Trends Genet. 2:9–13 (1986)). Heterozygotic mice are converted to homozygotes through mating.

In parallel, the heterozygotic mutant ES cells may also be converted to homozygotic cells in vitro, according to published protocols (for example, Mortensen et al., Mol. Cell. Biol. 12:2391–2395 (1992)), and used to generate homozygotic mice with the above described techniques. The homozygotic mice obtained by either method may be analyzed to determine the function of the knocked out gene of interest.

The MAGEKO Components

The MAGEKO process broadly encompasses three components: (i) the generation of gene mutations in mammalian genes using retroviral vectors; (ii) the production of libraries of knocked out genes which may be used to generate mutant animals; and (iii) the selection of cells carrying mutations in desired genes. Each of these components is now discussed.

(I) Components of the Retroviral Vectors

Retroviruses are RNA viruses which replicate through a DNA intermediate and which include as an obligatory step of their life cycle integration of the proviral DNA into the host chromosome (Varmus and Brown, Retroviruses. In *Mobile DNA* (ed. Berg, D. E. and M. M. Howe), pp. 53–108. American Society for Microbiology, Washington, D.C. (1989)). Following integration, the provirus is maintained as a stable genetic element in the infected cell and its progeny. Most or possibly all regions of the host genome are accessible to retroviral integration (Withers-Ward et al., Genes Dev. 8:1473–1487 (1994)), and the above properties make retroviruses invaluable as both potent mutagens and chromosomal markers.

The MAGEKO process employs one or more retroviral vectors as mutagens. The principal vector is preferably based on the Moloney murine leukemia virus (MoMLV) (Varmus and Brown, supra). Secondary vectors are of different retroviral origin and include, for example, lentiviral (Vannus and Brown, supra) or avian leukosis-sarcoma virus (ALV) (Varmus and Brown, supra) based vectors. Different retroviral backbones are utilized in the MAGEKO technique to increase the number of genes that are affected by insertional mutagenesis, on the theory that different retroviruses may have different genomic targeting preferences. Furthermore, in the case of the lentiviral vectors, it is known that this retrovirus is capable of transducing nondividing cells (Naldini et al., Science 272:263–267 (1996)), thus allowing for earlier detection of infected cells. Integration of vectors involving MoMLV depends on mitosis (Roe et al., EMBO J. 12:2099–2108 (1993)).

Each vector used in the mutagenesis procedure is quite similar, differing significantly only in the retroviral backbone sequence. Otherwise, the vectors carry in common several unique features essential to the subsequent functional characterization of the inactivated genes of interest. In particular, as discussed in more detail below, each of the vectors is highly mutagenic, each allows rapid identification of infected cells, and each allows specific detection of cells expressing the gene with the retroviral insertion. Moreover, the vectors specifically mark cells expressing the mutant gene, allow temporal and spatial analysis of the phenotype of the disrupted gene, provide for conditional tissue-specific gene inactivation, facilitate the conditional ablation of cell lineages expressing the mutant gene, and facilitate conditional ectopic expression of any gene in any desired tissue. Other important attributes of these vectors include the ability to generate animals with conditional tumors of any cell origin as well as the ability to establish conditional immortal cell lines of any cell type.

Figure 1:
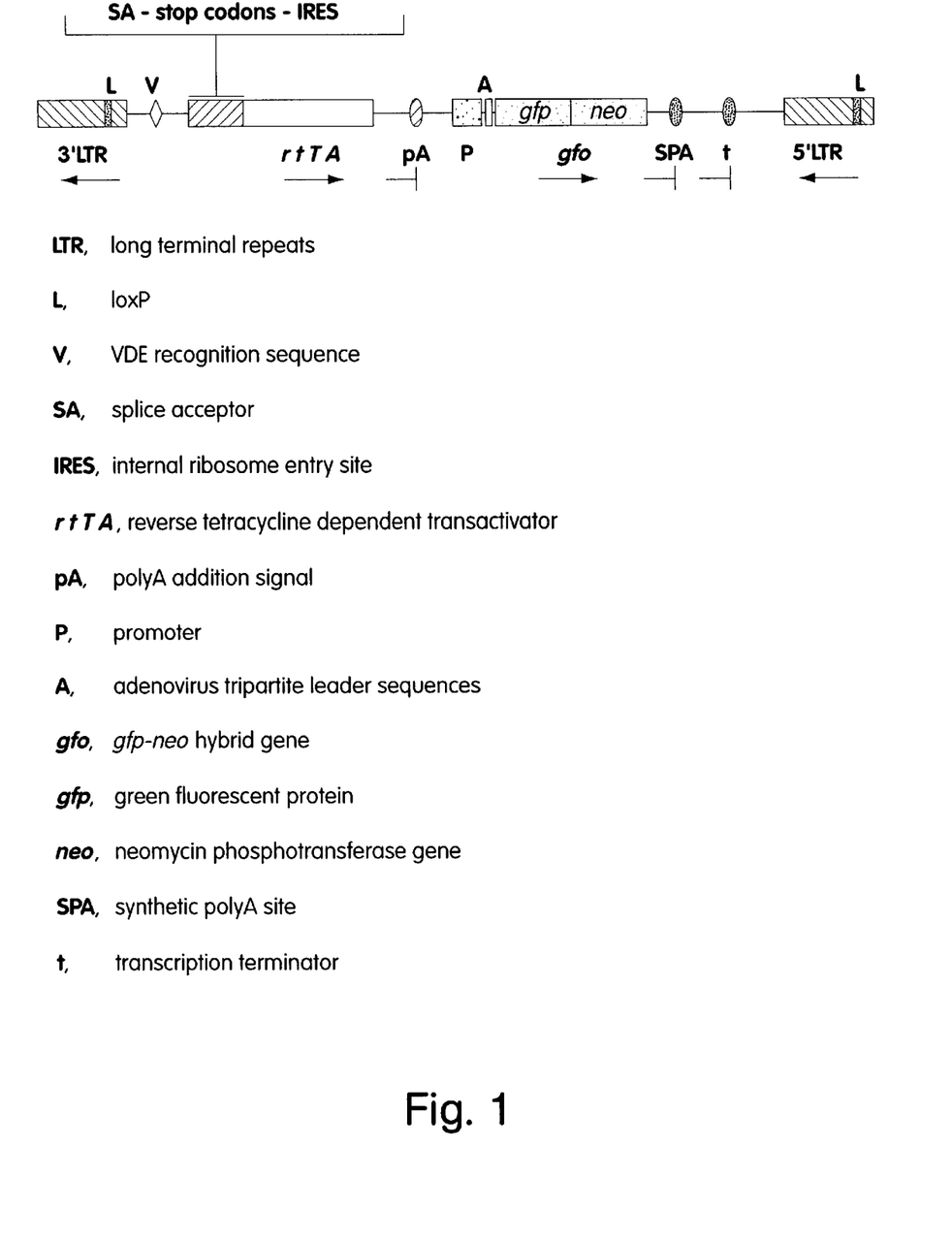
FIG. 1 is a schematic representation of a Moloney murine leukemia virus (MoMLV)-based vector for use in the MAGEKO process.

FIG. 1 depicts the MoMLV-based retroviral vector and its various features. The orientation of the transcriptional units is indicated by arrows. Vectors of other retroviral origin are quite similar to the MoMLV-based vector, differing only in the sequences of the retroviral backbone. The origin and importance of the elements are as follows.

(a) Retroviral Sequences. The retroviral sequences are necessary for packaging and random integration of the incoming DNA into the host genome. The MoMLV sequences are substantially similar to the sequences found in the vector pGen⁻ (Soriano et al., J. Virol. 65:2314–2319 (1991)), a vector which lacks the viral enhancer sequences and which contains the bacterial supF gene positioned in the 3' long terminal repeats (LTR). Upon integration into the genome, the 5'LTR enhancer sequences are also deleted, and the supF sequences are copied to the 5'LTR. As described below, the viral LTRs of the parental vector are modified to contain loxP sequences. In addition, the trancriptional orientation of all non-retroviral vector sequences are inverted relative to the transcriptional orientation of the 5' LTR promoter (FIG. 1). Production of high titer stocks from this vector are accomplished following published procedures (for example, Soneoka et al., Nucleic Acids Res. 23:628–633 (1995); Yee et al., Proc. Natl. Acad. Sci. USA 91:9564–9568 (1994); and Mann et al., Cell 33:153–159 (1983)). Alternative retroviral sequences may, for example, be derived from or based upon any lentiviral or ALV vector, and appropriate standard techniques may be used for viral propagation.

(b) LoxP. The loxP sequence is the recognition sequence of the bacteriophage P1 CRE recombinase, and its use is described in Sauer, Meth. Enzymol. 225:890 (1993). This sequence mediates recombinational excision of the retroviral insertion in the presence of CRE. It also facilitates targeted chromosomal rearrangements, such as translocations and deletions (Ramirez-Solis et al., Nature 378:720–724 (1995)) in cells containing more than one provirus. Such cells may be obtained through mating of mice, each carrying a different loxP-tagged retroviral insertion. Alternatively, FRT, the recognition sequence of the *Saccharomyces cerevisiae* FLP recombinase (Dymecki, Proc. Natl. Acad. Sci. 93:6191–6196 (1996)) may be used for this purpose, and recombinational excision may be mediated by the FLP protein.

(c) V. V, or VDErs, is the recognition sequence of the VDE DNA endonuclease from *Saccharomyces cerevisiae* (Bremer et al., Nucleic Acids Res. 20:5484 (1992)). This sequence provides a unique chromosomal marker. Other chromosomal markers may also be utilized for this purpose.

(d) Splice Acceptor. As shown in FIG. 1, a consensus splice acceptor sequence is also included in the retroviral vectors. This sequence is required for fusion of the retroviral transcripts to the endogenous gene transcript in situations where the retroviral integration occurs in an intron. The splice acceptor site prevents the retroviral transcript from being inadvertently spliced out of the genome, thereby maximizing the likelihood that an insertion is mutagenic for the endogenous gene (Gossler et al., Science 244:463–465 (1989); Friedrich and Soriano, Genes Dev. 5:1513–1523 (1991); Skames et al., Genes Dev. 6:903–918 (1992); Takeuchi et al., Genes Dev. 9:1211–1222 (1995); Wurst et al., Genetics 139:889–899 (1995); Forrester et al., Proc. Natl. Acad. Sci. USA 93:1677–1682 (1996); and Brenner et al., Proc. Natl. Acad. Sci. USA 86:5517–5521 (1989)). A preferable consensus splice acceptor is derived from the Adenovirus major late transcript (Robberson et al., Mol. Cell. Biol. 10:84–94 (1990)), but any other splice acceptor sequence may be utilized in the vectors of the invention.

(e) Stop Codons. Nonsense codons in all three reading frames ensure translational termination in the gene with the retroviral insertion. Any nonsense codon or set thereof may be used for this purpose.

(f) IRES. The internal ribosome entry site provides for translation initiation of the tag gene (described below). As shown, a preferred IRES is derived from the Encephalomyocarditis virus (Morgan et al., Nucleic Acids Res. 20:1293–1299 (1992)). Other appropriate ribosome entry sites may also be used in the present vectors.

Figure 3:
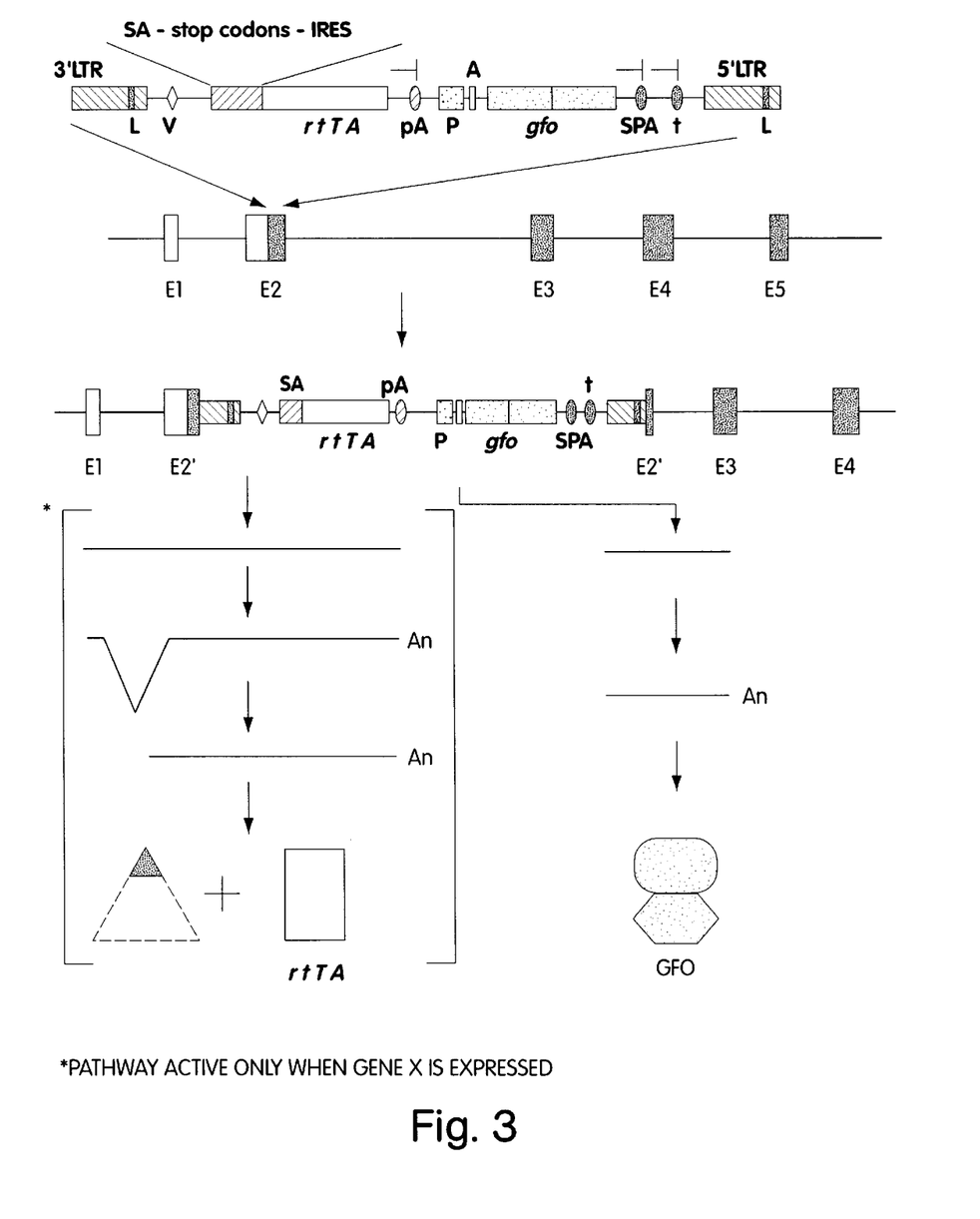
FIG. 3 is a schematic representation of the MAGEKO process of insertional mutagenesis in an exon sequence.
Figure 4:
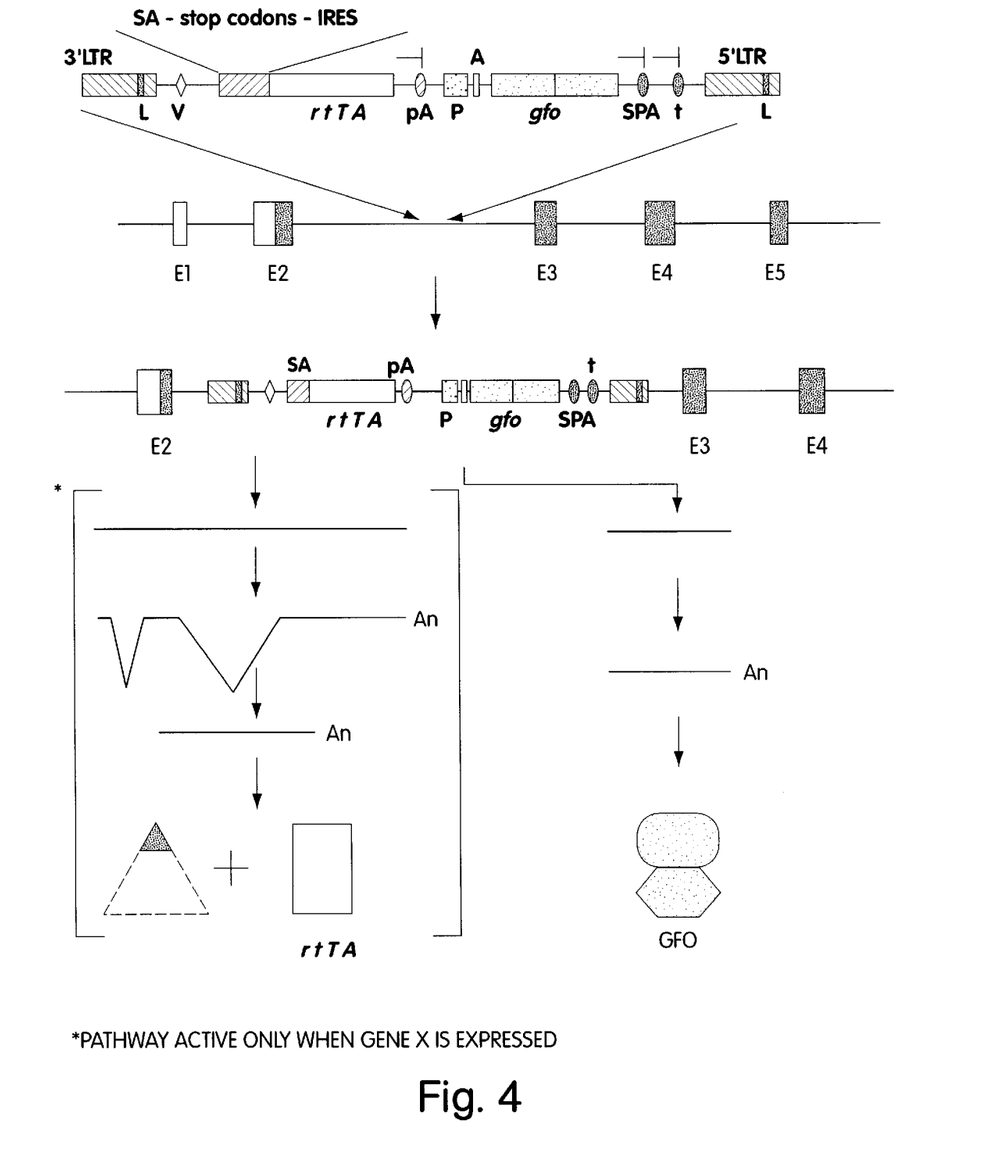
FIG. 4 is a schematic representation of the MAGEKO process of insertional mutagenesis in an intron sequence.

(g) rtTA. The sequence indicated as "rtTA" in FIG. 1 is preferably a hybrid protein composed of a mutant tetracycline repressor and the VP16 transcription activation domain (Gossen et al., Science 268:1766–1769 (1995)). rtTA possesses the ability to stimulate expression of genes placed under the control of the tetracycline operator in the presence of tetracycline derivatives (Gossen et al., Science 268:1766–1769 (1995)). In the present invention, rtTA is expressed under the control of the promoter of the endogenous cellular gene which has been mutated by the retroviral insertion (FIGS. 3 and 4). Conditionally expressed rtTA is a key component to functional characterization of genes facilitated by the MAGEKO approach.

(h) A. As shown in FIG. 1, the vectors of the invention also include a polyA addition signal. This signal is required for the processing and expression of the rtTA mRNA. One preferred pA sequence is derived from the bovine growth hormone gene (Goodwin and Rottman, J. Biol. Chem. 267:16330–16334 (1992)), although any other polyadenylation signal may be used. Examples of other useful pA sequences include, without limitation, the insulin and SV40 pA sequences.

(i) P. P is the constitutively expressed mouse phosphoglycerate kinase-b 1(PGK) promoter (Adra et al., Gene 60:65–74 (1987)). This promoter is required for the expression of GFO (described below). Other constitutive mammalian promoters may be used in place of the PGK sequence.

j) ATL. ATL, or the adenovirus tripartite leader sequence (Sheay et al., BioTechniques 15:856–862 (1993)), is included in the vector as a cis-acting inducer of gene expression. This sequence enhances production of GFO. Other leader sequences may be substituted for ATL.

(k) gfo. A hybrid gfo gene is included in the vectors. This gene is composed of a mutant GFP at the 5' end and neomycin (NEO) coding sequences at the 3' end. GFP mutants are derivatives of the *Aequorea victoria* GFP, an autofluorescent protein widely used as a reporter of gene expression (Chalfie et al., Science 263:802–805 (1994); and Pahn et al., Nature Structural Biology 4:361–365 (1997)). Preferred mutants encode a green fluorescent protein with increased cellular fluorescence and include, without limitation, a GFP sequence which is based on the sequence of Heim et al. (Current Biology 6:178–182 (1996)) but which includes at least one of the following mutations: P4-3 (Y66H, Y145F), W7 (Y66W, N146I, M153T, V163A, N212K), SG11 (F64L, I167T, K238N), SG25 (F64L, S65C, U167T, K238N), or SG50 (F64L, Y66H, V163A). The gfo sequence is used for fluorescence activated cell sorting (FACS) of infected ES cells, an important step in the generation of LOKs. The neo gene codes for bacterial neomycin phosphotransferase (Southern and Berg, J. Mol. Appl. Gen. 1:327–341 (1982)). Expression of this sequence renders ES cells which contain the provirus resistant to G418. Neomycin resistance is used in the methods of the invention to select ES cells which are homozygotic for the proviral insertion; this is accomplished by increasing the concentration of G418 in the cell culture medium, as previously described (Mortensen et al., Mol. Cell. Biol. 12:2391–2395 (1992)). Other detectable and selectable markers may also be utilized in the invention.

(l) SPA. A synthetic polyA addition signal is also included in the vector to facilitate processing and expression of the gfo mRNA (Levitt et al., Genes Dev. 3:1019–1025 (1989)). Other synthetic or natural poly A sequences may be utilized.

(m) t. Transcriptional termination sequences are an important feature of the retroviral vectors. These sequences terminate transcription from both the PGK and the cellular promoters. Appropriate transcription termination results in a considerably increased mutagenic potential of the retroviral insertion and a decrease in the abnormal expression of genes adjacent to the provirus; this eliminates potential complications in the phenotypic characterizations of KO mice, as has been observed in some instances (Olson et al., Cell 85:1–4 (1996)). As shown in FIG. 1, a preferred termination sequence is derived from the human complement gene (Ashfield et al., EMBO J. 10:4197–4207 (1991)), but any other appropriate transcription termination sequence may be utilized.

(II) Unique Properties of and Uses for the Retroviral Vectors of the Invention

The vectors of the invention possess a number of unique properties, making them useful for various types of gene disruption methods and types of analyses. Examples of these unique properties and uses now follow.

The retroviral vectors are highly mutagenic. One significant advantage provided by the present retroviral vectors is the fact that these vectors are highly mutagenic. This property arises, at least in part, because the vectors contain a combination of a consensus splice acceptor and transcriptional termination sequences. The splice acceptor has been previously described (Gossler et al., Science 244:463–465 (1989); Friedrich and Soriano, Genes Dev. 5:1513–1523 (1991); Skames et al., Genes Dev. 6:903–918 (1992); Takeuchi et al., Genes Dev. 9:1211–1222 (1995); Wurst et al., Genetics 139:889–899 (1995); Forrester et al., Proc. Natl. Acad. Sci. USA 93:1677–1682 (1996); and Brenner et al., Proc. Natl. Acad. Sci. USA 86:5517–5521 (1989)), but the combination with termination sequences is novel, and this combination is important for the elimination of read-through transcription which is frequently observed in cellular sequences flanking proviruses (Swain and Coffin, Science 255:841–845 (1992)). The termination sequence also enhances mutagenicity by blocking potential bypassing of the insertion by alternative splicing mechanisms which make use of fortuitous chromosomal splice sites; these sites are inaccessible due to transcription termination at t.

Figure 2:
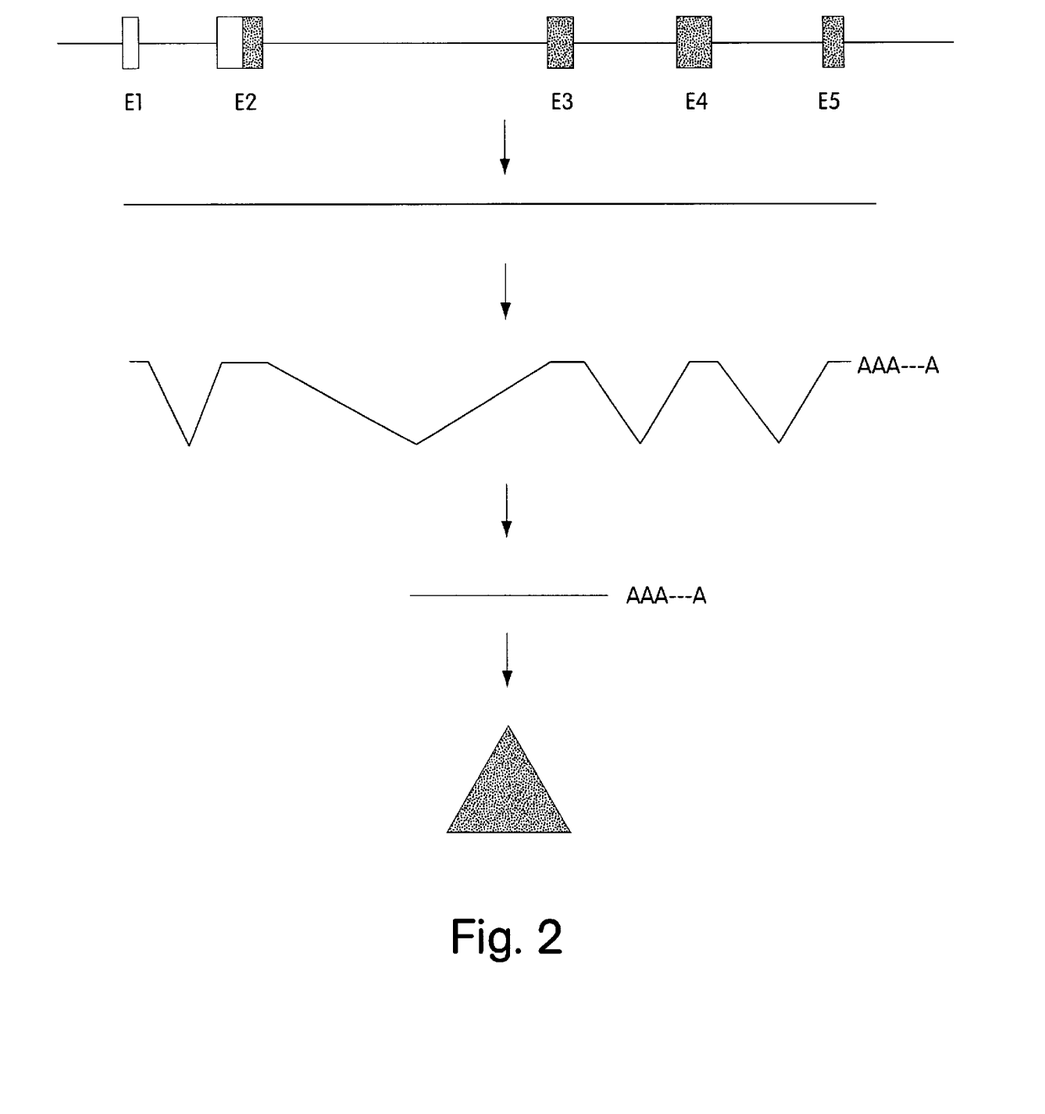
FIG. 2 is a schematic representation of an insertional mutagenesis event.

Insertion of the retroviruses into a gene of interest, for example, gene X in FIGS. 2–4, leads to gene inactivation which is independent of the site of integration. Normal transcription and subsequent translation of gene X (FIG. 2) are disrupted, whether or not the retroviral insertion has occurred in an exon sequence (FIG. 3) or an intron sequence (FIG. 4). This advantage is quite important. Although gene disruption is generally expected following integration of standard retroviruses into exons, the outcome of retroviral integration into introns is less predictable, and only a small fraction of retroviral insertions have been found to be associated with recessive phenotypes in the mouse (Jaenisch, Science 240:1468–1474 (1988)). Accordingly, the combination of a splice acceptor sequence and a transcriptional terminator is an important feature of the present invention, rendering the presently described vectors highly mutagenic even when integrated at intron locations.

The MAGEKO method allows rapid identification of infected cells. In a second advantage, the invention allows rapid identification of infected cells. As described above, the vectors of the invention include a marker which facilitates the identification of vector-containing cells. In one embodiment, the vectors carry a GFP mutant with increased cellular fluorescence linked to the PGK promoter. This marker allows for the identification of infected cells hours after infection, thus enabling the rapid sorting of transduced cells, for example, by FACS analysis. This is an important element for the generation of LOKs.

The MAGEKO approach provides for specific detection of cells expressing the mutant gene. As described above, the fusion gene, rtTA, is produced only in cells expressing the gene mutated by a retroviral insertion. The conditional nature of rtTA synthesis allows the specific tagging of insertion-containing cells through a binary mammalian system, such as a binary mouse system. According to this technique, mice carrying the retroviral vector of the present invention may be mated to mice containing a marker gene under the control of the rtTA-dependent promoter. In offspring containing both transgenes, that marker will only be produced in cells expressing rtTA, and only in the presence of tetracycline derivatives. As a result, the only cells in the offspring which synthesize the marker are those cells in which the gene mutated by the provirus is expressed. These cells, depending on the nature of the marker, may then be detected and, if desired, separated from the remaining cells using standard techniques. The marker may be any reporter of gene expression. Such reporters include, without limitation, the bacterial lacZ gene (An et al., Mol. Cell. Biol. 2:1628–1632 (1982)), green fluorescent protein, wavelength variations of green fluorescent protein (Heim et al., Proc. Natl. Acad. Sci. USA 91:12501–12504)), luciferase (de Wet et al., Mol. Cell. Biol. 7:725–737 (1987)), and chloramphenicol acetyltransferase (CAT) (Gorman et al., Mol. Cell. Biol. 2:1044–1051 (1982)).

The MAGEKO process facilitates conditional ablation of cell lineages expressing mutant genes. The use of the rtTA construct facilitates the ability to conditionally ablate cell lineages expressing mutant genes. Cell ablation studies are instrumental in assigning function to entire cell lineages, as has been demonstrated in several instances (Breitman et al., Science 238:1563–1565 (1987); Behringer et al., Genes Dev. 2:453–461 (1988); Landel et al., Genes Dev. 2:1168–1178 (1988); Breitman et al., Development 106:457–463 (1989); Heyman et al., Proc. Natl. Acad. Sci. USA 86:2698–2702 (1989); Borrelli et al., Nature 339:538–540 (1989); Breitman et al., Mol. Cell. Biol. 10:474–479 (1990); Kunes and Steller, Genes Dev. 5:970–983 (1991); Moffat et al., Development 114:681–687 (1992); Nirenberg and Cepko, J. Neurosci. 13:3238–3251 (1993); and Dzierzak et al., Intern. Immunol. 5:975–984 (1993)). The retroviral vectors of the present invention are designed to utilize this powerful approach.

According to this aspect of the invention, conditional cell ablation is accomplished through a binary transgenic mouse system. In this system, a mouse that contains the "weapon" transgene in a silent form is mated to a mouse that expresses the activator. In the offspring that inherit both transgenes, the "weapon" is activated, and it exerts its killing effects only in cells expressing the activator. In the context of the rtTA system, mice expressing rtTA under the control of the endogenous mouse gene promoter synthesize rtTA only in cells expressing the mutant gene (FIGS. 3 and 4). These mice are mated with mice carrying conditionally produced "cell ablation factors" which are themselves synthesized only in the presence of both rtTA and tetracycline derivatives. Offspring containing both transgenes are subjected to cell ablation studies following administration of tetracycline derivatives and resultant destruction of cells expressing the gene with the retroviral insertion. Examination of these offspring provides a functional characterization of the ablated cell lineage.

Conditionally produced "cell ablation factors" useful in the invention include, but are not limited to, wild-type and mutant toxins (Borrelli et al., Nature 339:538–540 (1989); Frankel et al., Mol. Cell. Biol. 9:415–420 (1989); and Frankel et al., Mol. Cell. Biol. 10:6257–6263 (1990)), wild-type and mutant herpes simplex virus thymidine kinases (HSV-tk) (Salomon et al., Mol. Cell. Biol. 15:5322–5328 (1995); and Black et al., Proc. Natl. Acad. Sci. USA 93:3525–3529 (1996)), and apoptotic proteins such as the Drosophila reaper gene product (White et al., Science 271:805–807 (1996)). If an HSV-tk gene is utilized, gancyclovir, in addition to tetracycline derivatives, is administered to trigger cell killing. In another example, conditionally produced β-galactosidase may also be used to facilitate cell ablation, as shown for various cell types in the nervous system (Nirenberg and Cepko, J. Neurosci. 13:3238–3251 (1993)).

Use of MAGEKO for temporal and spatial phenotypic analysis of disrupted genes. Use of the methods of the invention and, for example, the rtTA construct, also facilitates the temporal and spatial characterization of the phenotypes of disrupted genes. In many instances, especially if the insertional mutation in the homozygotic state is lethal or results in a phenotype interfering with further analysis (Copp, Trends Genet. 11:87–93 (1995)), it is preferable to inactivate a gene of interest in an animal in a temporal and spatial manner. In the present invention, this is accomplished through the use of mosaic animals derived from a mixture of ES cells, some of which are heterozygotic and some of which are homozygotic for mutations in the gene of interest.

In these mosaic animals, the heterozygotic cells rescue those cells which are homozygotic, as has been generally demonstrated previously (Nagy and Rossant, J. Clin. Invest. 97:1360–1365 (1996); and Robb et al., EMBO J. 15:4123–4129 (1996)), and this leads to the generation of mosaics.

According to this aspect of the invention, mosaic mice are generated from homozygotic mutant ES cells in the gene of interest with mutant ES cells containing the identical proviral insertion in only one of the two alleles of the same gene. The heterozygotic cells (derived from animals generated as described above for the conditional ablation technique) also contain conditionally produced "cell ablation factors." These factors are synthesized only in the presence of both rtTA and tetracycline derivatives, and rtTA, in turn, is produced only in cells expressing the gene with the retroviral insertion (FIGS. 3 and 4).

Administration of tetracycline derivatives to mosaic animals leads to the specific obliteration of heterozygotic cells in which the mutant gene is expressed, due to the presence of the "ablation factors" in those cells only. As a result, the cell population of an animal expressing the mutant gene will be exclusively composed of homozygotic mutant cells. Under these conditions, the phenotype associated with the gene of interest may be assessed. This approach is useful for the phenotypic analysis of mutants, particularly when generation of adult mice is compromised in the homozygotic state.

Use of the MAGEKO process for conditional tissue-specific gene inactivation. In some instances, temporal and spatial phenotypic analysis of a disrupted gene may not be adequate to assign gene function. To address this problem, a different but complementary approach, termed conditional tissue-specific gene inactivation, may be employed. According to this approach, a gene of interest is inactivated, when desired, in the cells in which it is expressed. This general technique has been previously used to assign gene functions through the use of tissue-specific gene targeting (Gu et al., Science 265:103–106 (1994); Kuhn et al., Science 269:1427–1429 (1995); and Rajewsky et al., J. Clin. Invest. 96:600–603 (1996)).

Conditional tissue-specific gene inactivation is accomplished through a binary transgenic mouse system, similar in principle to the one described above for conditional ablation of cell lineages. Here, the mating partner carrying the "activator" is derived from heterozygotic mutant ES cells containing a retroviral insertion in one of the two alleles of the gene to be subjected to the conditional tissue-specific inactivation. This mouse produces rtTA only in cells synthesizing the target gene (FIGS. 3 and 4). the other mating partner, i.e., the one with the silent "weapon," carries a conditionally expressed ribozyme and a conditionally expressed recombinase.

Ribozymes are molecules capable of catalyzing sequence specific cleavage of targeted RNAs (Altman, Proc. Natl. Acad. Sci. USA 90:10898–10900 (1993)). In this system, the ribozyme is preferably expressed using an RNA polymerase III (Pol III) dependent promoter, such as the U6 small nuclear RNA promoter (Das et al., EMBO J. 7:503–512 (1988)). The Pol III promoter synthesizes the appropriate ribozyme only in the presence of rtTA and tetracycline derivatives. In addition, the constitutive Pol III promoter is preferably separated by transcription terminators from the ribozyme sequences. Each ribozyme is specifically designed to target and inactivate the gene of interest (according to published protocols, for example, by Altman, Proc. Natl.

Acad. Sci. USA 90:10898–10900 (1993); and Liu and Altman, Genes Dev. 9:471–480 (1995)). The presence of the terminators blocks downstream transcription (Das et al., EMBO J. 7:503–512 (1988)) and thus interferes with the synthesis of the ribozyme. The terminator sequences are flanked by FRT or loxP (i.e., the recognition sequence of either the *Saccharomyces cerevisiae* Flp recombinase (Dymecki, Proc. Natl. Acad. Sci. USA 93:6191–6196 (1996)) or the bacteriophage PI CRE recombinase (Sauer, Methods Enzymol. 225:890–900 (1993))). Flp or CRE is expressed only in the presence of rtTA and tetracycline derivatives.

In offspring containing both transgenes, Flp or CRE is produced in cells expressing the target gene when tetracycline derivatives are administered to the animal. Production of Flp or CRE leads to recombinational excision of the termination sequences and synthesis of the ribozyme in those cells. As a result, the target gene is subjected to ribozyme action, and the phenotype of this conditional tissue-specific gene inactivation event is amenable to analysis.

Another approach for conditional tissue-specific gene inactivation is based on conditional functional complementation between the disrupted and wild type alleles of the mouse gene or between the disrupted mouse gene and its wild type human homolog. This is a two step procedure that first involves mating of heterozygotic mice carrying the retroviral sequences of the present invention integrated in a particular gene to heterozygotic mice containing an extra copy of the wild type version of this gene under the rtTA-dependent promoter. Crossing F1 offspring containing both transgenes generate mice that are homozygotic in the disrupted gene but that also carry the wild type allele under the rtTA-dependent promoter. As a result, in the F2 mice, the wild type allele is expressed in the presence of tetracycline derivatives in the same cells that express the mutant gene. The presence of the wild type gene rescues the mutant phenotype which, in turn, may be assessed, when desired, upon withdrawal of the tetracycline derivatives. The very same approach may be used to complement the disrupted mouse gene with its human homolog, which is then expressed in the same cells that express the mouse mutant gene. If a human disease state gene is utilized in this technique, the F2 mice obtained may be used as animal models of the human disease, for example, to study the disease or isolate or identify therapeutic compounds.

Use of the MAGEKO process for conditional ectopic expression of the gene of interest in any desired tissue. Targeted gene expression is a powerful method for assigning function to genes, as has been demonstrated in several instances (Balling et al., Cell 58:337–347 (1989); Kessel et al., Cell 61:301–308 (1990); Brand and Perrimon, Development 118:401–415 (1993); and Halder et al., Science 267:1788–1792 (1995)). The retroviral vectors of the present invention are designed to utilize this powerful approach. According to this aspect of the invention, conditional targeted expression of a gene of interest is accomplished through a binary transgenic mouse system, similar to those described above. Again, in this system, one mating partner expresses rtTA under the control of the promoter associated with the gene having the retroviral insertion; as such, rtTA is synthesized only in cells expressing the mutant gene (FIGS. 3 and 4). The other mating partner contains the gene of interest and synthesizes this gene product conditionally, i.e., only in the presence of both rtTA and tetracycline derivatives. In offspring having inherited both transgenes, the gene of interest is specifically expressed only in cells where the gene having the retroviral insertion is expressed, and only in the presence of tetracycline derivatives. The physiological consequences of this conditional targeted gene expression is thereby amenable to analysis in the offspring.

Importantly, this approach provides an unlimited number of different target tissues for analysis; in theory, every tissue in the animal can be selected, if desired, to study the consequences of the conditional ectopic expression of a gene of interest.

MAGEKO allows establishment of animals with conditional tumors in any desired cell The binary transgenic mouse system is also useful for the generation of animals with conditionally induced tumors. Here, one mating partner expresses rtTA under the control of the promoter of the gene with the retroviral insertion, and thus synthesizes rtTA only in cells expressing the mutant gene (FIGS. 3 and 4). The other mating partner carries conditionally produced "neoplastic factors," such as combinations of oncogenes (Bishop, Cell 64:235–248 (1991); and Hunter, Cell 64:249–270 (1991)) and (if necessary) other facilitating genes, such as telomerase (deLange, Proc. Natl. Acad. Sci. USA 91:2882–2885 (1994); Counter et al., Proc. Natl. Acad. Sci. USA 91:2900–2904; and Sharma et al., Proc. Natl. Acad. Sci. USA 92:12343–12346 (1995)). These factors are synthesized only in the presence of both rtTA and tetracycline derivatives. Accordingly, offspring containing both transgenes develop tumors in the cells expressing the gene with the retroviral insertion upon administration of tetracycline derivatives.

This approach affords a number of advantages over previous methodologies for the generation of transgenic mouse models for neoplasia (Quaife et al., Cell 48:1023–1034 (1987); Sinn et al., Cell 49:465–475 (1987); Jat et al., Proc. Natl. Acad. Sci. USA 88:5096–5100 (1991); and Sandmoller et al., Cell Growth and Diff. 6:97–103 (1995)). First, the method is not limited by the restricted spectrum of available tissue-specific promoters. And, second, the oncogenic state is not constitutive, but is conditional; the neoplastic transformation of a normal mouse tissue is initiated only in the presence of tetracycline derivatives, making the system more amenable to analysis. Animals generated by this method provide information about the types of oncogenes which play roles in particular cell types, and may also be used as animal models to screen anti-cancer therapies.

MAGEKO allows establishment of conditional immortal cell lines of any desired type. Once available, animals with developed tumors of desired cellular origin (produced as described above) are an immediate source of tumor cell lines. In the alternative, immortal cell lines can be established from these animals prior to tumor development, simply by isolating the desired cells from the animals and culturing in vitro in the presence of tetracycline derivatives.

Such cell lines provide a valuable reagent for high throughput drug screening procedures to identify compounds which affect the gene with the retroviral insertion. In particular, since these cell lines express the target gene and also constitutively synthesize GFP, the cell lines are, for example, GFP$^+$, β-GAL$^+$ (if β-GAL is the reporter gene). Any drug that specifically affects the gene in question produces GFP$^+$, β-GAL$^-$ cells.

(III) LOK

The retroviral vectors described above are used to construct libraries of ES cells containing knock outs in endogenous genes or "LOKs". To produce these libraries, the vectors are introduced by infection into ES cells to obtain insertions, on the average, every 1 Kb in the genome. The LOK preferably consists of thirty million such insertions, each carrying an independent provirus. The complexity of an LOK is high enough that most mouse genes should statistically be hit at least once by an independent retroviral integration event.

Following infection of ES cells with the retroviral vectors, transduced cells expressing the visual marker (for example, GFP) are selected by FACS analysis, and the cells are distributed in multi-well plates. The contents of combinations of wells are then pooled, subsequent to duplicate formation and storage of the replica, and appropriate matrices are generated to facilitate assignment of a specific cell to a particular well. Several proposed and established pooling strategies are available for the generation of the desired matrix to screen the LOK (see, for example, Zwaal et al., Proc. Natl. Acad. Sci. USA 90:7431–7435 (1993); Evans and Lewis, Proc. Natl. Acad. Sci. USA 86:5030–5034 (1989); Green and Olson, Proc. Natl. Acad. Sci. USA 87:1213–1217 (1990); Kwiatkowski et al., Nucleic Acids Res. 18:7191–7192 (1990); and Barillot et al., Nucleic Acids Res. 19:6241–6247 (1991)).

(IV) KIS

The present invention also includes a gene Knock out Identification System (or "KIS"). According to this aspect of the invention, genomic DNA, including the integrated nucleic acids of the retroviral vectors, are isolated from the pooled ES cells of the LOK and are fragmented. These fragments are then circularized and amplified by inverted PCR (see, for example, Ochman et al., Genetics 120:621–625 (1988); and Triglia et al., Nucleic Acids Res. 16:8186 (1988)), using primers which hybridize to the retroviral vector sequences but which are not present in the mouse genome; this method has been successfully applied to the detection of retroviral insertions in the Zebrafish genome (Allende, Genes Dev. 10:3141–3155 (1996)), P element insertions in the Drosophila genome (Dalby et al., Genetics 139:757–766 (1995)) and transposon insertions in the Arabidopsis genome (Sundaresan et al., Genes Dev. 9:1797–1810 (1995)). Alternatively, modifications of inverse PCR, such as oligo-cassette mediated PCR (see, for example, Rosenthal and Jones, Nucleic Acids Res. 18:3095–3096 (1990)) or ligation mediated PCR (see, for example, Mueller and Wold, Science 246:780–786 (1989)), may be used.

Genomic DNA fragments, once amplified, are transferred to hybridization supports, generating an ordered array of genomic DNA flanking the provirus. Labelled DNA from a gene of interest is then hybridized to the pooled genomic DNA, and a positive signal leads to the rapid identification of the desired ES cell clone.

Alternatively, detection of a retroviral integration site may be accomplished by direct sequencing of the amplified DNA of an ES clone; this approach, however, requires the isolation of single clones of ES cells and is preferably used only for a subset of the generated clones. In another alternative approach, an integration site may be determined by sequence detection using a positional oligonucleotide probing technique (POP), a method which is ideal for the processing of limited sequence information in parallel. According to this technique, all possible oligonucleotides of a specific length are synthesized in a high density array (such as an Affymetrix chip (see, for example, Lipshutz et al., BioTechniques 19:442–447 (1995)) and hybridized to the amplified DNA from ES cells. The POP technique is based on generating sequence information for an unknown region of nucleic acid (i.e., the genomic DNA), which is linked to a known sequence (i.e., a portion of the retroviral vector). Because retroviral integration is precise and results in the integration of a viral LTR within the genomic DNA, the LTR sequence is a preferred sequence for designing oligonucleotide probes. For example, oligonucleotides that contain 8 bases corresponding to the tip of the LTR and nine random bases can probe 4e9=262,144 combinations. This strategy of junction sequencing by oligonucleotide arrays can be used in place of, or in parallel with, the hybridization technique described above. As information about the mouse genome sequence increases, this sequence tag approach will become increasingly useful in identifying insertions in known genes.

Following identification of ES cell clones with desired mutations, heterozygous and homozygous mutant mice are generated by the procedures described above.

Other Embodiments

The techniques described herein are applicable to the generation of mutations in any appropriate non-human mammal. In particular examples, the techniques are useful for generating libraries of gene mutations, ES cells, and transgenic animals in any mammal which may be used as a disease model or any domesticated animal including, but not limited to, rodents (for example, mice, rats, and guinea pigs), cows, sheep, goats, rabbits, and horses.

Other embodiments are within the following claims.

What is claimed is:

1. A retroviral vector comprising (i) a splice acceptor sequence, (ii) a transcription terminator, at which site transcription terminates, and (iii) retroviral packaging and integration sequences.

2. The retroviral vector of claim 1, wherein said retroviral vector includes packaging and integration sequences from a Moloney murine leukemia virus sequence.

3. The retroviral vector of claim 1, further comprising a regulatory gene positioned for expression under the control of an endogenous promoter in a mammalian cell, wherein said promoter is operably linked to said regulatory gene upon integration of said vector into the genome of said mammalian cell.

4. The retroviral vector of claim 3, wherein said regulatory gene encodes a regulatory protein that modulates the expression of another gene.

5. The retroviral vector of claim 4, wherein said regulatory protein is a tetracycline repressor fused to an activator protein.

6. The retroviral vector of claim 5, wherein said activator protein is VP16.

7. The retroviral vector of claim 1, further comprising a DNA sequence encoding a constitutively expressed marker gene, wherein said marker gene encodes a marker protein detectable in a mammalian cell.

8. The retroviral vector of claim 7, wherein said marker protein is a green fluorescent protein.

9. The retroviral vector of claim 8, wherein said green fluorescent protein has increased cellular fluorescence relative to the wild-type green fluorescent protein.

10. The retroviral vector of claim 8, wherein said green fluorescent protein is fused to a mammalian selectable marker protein.

11. The retroviral vector of claim 10, wherein said mammalian selectable marker protein is neomycin phosphotransferase.

12. The retroviral vector of claim 1, further comprising a recognition sequence recognized by a yeast VDE DNA endonuclease.

13. The retroviral vector of claim 1, further comprising a sequence which is recognized by a recombinase enzyme.

14. The retroviral vector of claim 13, wherein said sequence is a loxP sequence.

15. A cell containing a retroviral vector of claim 1.

* * * * *

UNITED STATES PATENT AND TRADEMARK OFFICE
CERTIFICATE OF CORRECTION

PATENT NO. : 6,228,639 B1
DATED : May 8, 2001
INVENTOR(S) : George A. Gaitanaris It is certified that error appears in the above-identified patent and that said Letters Patent is hereby corrected as shown below:

Column 2,
Line 13, change "Skames" to -- Skarnes --;

Column 5,
Line 21, change "ribozyne" to -- ribozyme --;

Column 8,
Line 21, change "Skames" to -- Skarnes --;
Line 54, change "(h) A." to -- (h) pA. --;
Line 64, change "kinase-b 1 (PGK)" to -- kinase-1 (PGK) --;

Column 9,
Line 12, change "Pahn et al." to -- Palm et al. --;
Line 20, change "U167T" to -- I167T --;
Line 67, change "Skames" to -- Skarnes --;

Column 13,
Line 9, change "PI" to -- P1 --;
Line 10, change "(1993)))" to -- (1993)) --;

Column 14,
Line 12, change "cell" to -- cell type --.

Signed and Sealed this

Eleventh Day of June, 2002

*Attest:*

*Attesting Officer*

JAMES E. ROGAN
*Director of the United States Patent and Trademark Office*